United States Patent [19]

Russell et al.

[11] Patent Number: 4,517,390

[45] Date of Patent: May 14, 1985

[54] HYDROGENATION OF OLEFINS AND ALDEHYDES

[75] Inventors: Michael J. H. Russell, Reading; Barry A. Murrer, Henley on Thames, both of England

[73] Assignee: Johnson Matthey Public Limited Company, London, England

[21] Appl. No.: 580,294

[22] Filed: Feb. 21, 1984

Related U.S. Application Data

[63] Continuation of Ser. No. 361,051, Mar. 23, 1982, abandoned.

[30] Foreign Application Priority Data

Mar. 25, 1981 [GB] United Kingdom ............... 8109303

[51] Int. Cl.$^3$ ..................... C07C 29/14; C07C 5/03
[52] U.S. Cl. ................................ 568/881; 525/338; 585/269; 585/277
[58] Field of Search ............... 568/881; 585/269, 277; 525/338

[56] References Cited

U.S. PATENT DOCUMENTS 3,535,382 10/1970 Brown et al. ............... 260/690
3,766,279 10/1973 Fenton ........................ 568/881
3,992,432 11/1976 Napier et al. ................ 568/852

FOREIGN PATENT DOCUMENTS 2070023 9/1981 United Kingdom ............... 525/338

OTHER PUBLICATIONS

Dror and Manassen (J. Mol. Catal., 1976/7, 2, 219).
Dror and Manassen (Stud. Surf. Sci. Catal., 1981, 7B, 887).
Borowski et al., (Nouv. J. Chem., 1976, 2, 137).
B. R. James, "Homogeneous Hydrogenation", (Wiley), 1974.
Dehmlow, "Chemtech", Apr. 1975, 210-218.
J. Org. Chem. 1980, 45, 3860-3865, by Daniel L. Reger et al., Hydrogenation of Conjugated Dienes.

*Primary Examiner*—J. E. Evans
*Attorney, Agent, or Firm*—Cushman, Darby & Cushman

[57] ABSTRACT

A catalytic process for hydrogenation of unsaturated organic compounds is carried out in a two-phase aqueous/organic medium, in which the catalytic complex is dissolved in the aqueous phase and to which is added an amphiphilic reagent to facilitate phase boundary crossing of dissolved species. Catalyst separation from reaction products is thereby rendered more efficient.

The catalytic complex is preferably formed in situ and contains a water-soluble phosphine ligand, preferably a hydroxy- or carboxy-aryl phosphine.

4 Claims, No Drawings

HYDROGENATION OF OLEFINS AND ALDEHYDES

This is a continuation of application Ser. No. 361,051 filed Mar. 23, 1982 now abandoned.

This invention relates to a process for the hydrogenation of an unsaturated organic compound and especially provides an improved two phase hydrogenation process in which separation and recovery of precious metal species used therein as a catalytic component is facilitated.

Hydrogenation of unsaturated organic componds such as olefins, aldehydes and ketones to yield alkanes or alcohols is a well known process which generally uses as catalyst or catalyst precursor a complex of rhodium or other precious metal and is carried out in the organic phase. The complex is, in homogeneous hydrogenation reactions, soluble in the organic phase and difficulties ensue in separation and recovery of species present in the reaction mixture, especially used catalytic metal species.

There has in the past been a proposal to carry out hydrogenation processes in a two-phase system, in which a water-soluble catalytic or catalyst precursor complex is dissolved in an aqueous phase, the reactants and products being confined to the organic phase, so that the metal species is recoverable by separating the phases. Dror and Manassen (J. Mol. Catal., 1976/7, 2, 219) describes such a system for the hydrogenation of cyclohexene in which the water-soluble complex is a rhodium complex of sodium 3-sulphonatophenyldiphenylphosphine and a water-miscible co-solvent is used to attain a measurable rate of reaction. Borowski et al (Nouv. J. Chem., 1976, 2, 137) also used this complex for various two-phase hydrogenation reactions, avoiding the use of a co-solvent by utilising higher pressures of hydrogen. More recently, this complex has been used for the hydrogenation of naturally occurring phospholipids in aqueous solution (GB No. 1594603, published Aug. 5, 1981). The use of "surfactant ligands" of the type $Ph_2P(CH_2)_nCOO^-$ in aqueous micelles has also recently been proposed by Dror and Manassen (Stud. Surf. Sci. Catal., 1981, 7B, 887).

None of these proposals has provided a hydrogenation process which proceeds under mild conditions at an acceptable rate and in which the catalyst metal species is readily separable from the reaction product. Problems encountered include emulsification, catalyst elution to the organic phase and catalyst decomposition. Accordingly, it is an object of the present invention to provide an improved two-phase hydrogenation process which proceeds at an acceptable rate under mild conditions of temperature and pressure and which renders possible economic separation of catalyst metal species from the reaction product.

We have found that this object may substantially be achieved by including in the reaction medium a phase transfer agent or surfactant, which may conveniently be classes together as "amphiphilic reagents".

Accordingly, the invention provides a catalytic process for the hydrogenation of an unsaturated organic compound which comprises reacting together the said compound and hydrogen in the presence of a water-soluble complex of a platinum group metal in a reaction medium comprising an aqueous phase and an organic phase, wherein the reaction medium also includes an amphiphilic reagent.

Amphiphilic reagents may in general terms be regarded as compounds which have an affinity for both organic and aqueous phases. In the case of the process according to the invention, the presence of an amphiphilic reagent either increases the solubility of the complex in the organic phase relative to its solubility in the aqueous phase, or it increases the solubility of the unsaturated organic compound in the aqueous phase. Clearly, for good separation of metal catalyst species from products after reaction has taken place, there should be a tendency for the original phase constitution to be restored. Amphiphilic reagents may therefore preferably be regarded as compounds which facilitate passage of a species in either direction across a phase boundary between a medium in which it is relatively soluble and one in which it is relatively insoluble. Desirably, the amphiphilic reagent contains polar and non-polar moieties to provide the required affinity for both aqueous and organic phases, and should preferably be distributed principally in the aqueous phase with a minor portion in the organic phase. More preferably, the amphiphilic reagent should be substantially soluble in the aqueous and substantially insoluble in the organic, its effectiveness in operation being due, we believe, to its tendency to transport species across the phase boundary in view of the polar and non-polar moieties.

The amphiphilic reagent may be anionic, cationic or neutral. Many suitable reagents are available commercially as phase transfer reagents or surfactants. An example of a suitable anionic reagent is sodium dodecyl sulphate; an example of a neutral reagent is commercially-available "Brij 35" (ie $[C_{12}H_{25}(OCH_2CH_2)_{23}OH]$) and an example of a cationic reagent is a tetra-alkyl ammonium salt such as cetyltrimethylammonium bromide. Also useful as cationic reagents are other complex ammonium salts such as cetylpyridinium bromide, lauryl and myristyl ammonium bromides and cetyltrimethylammonium acetate.

The amphiphilic reagent should be present in a concentration relative to the platinum group metal of up to 100:1 on a molar basis, preferably from 1:1 to 25:1, for example 5:1 or 20:1. We have found in general that increasing quantities of amphiphilic reagent reduces the loss of platinum group metal species to the organic phase, although higher amounts tend to promote emulsification between the phases which results in difficulty in separating catalytic species.

The aqueous phase contains the water-soluble complex of platinum group metal, which preferably contains a water-soluble phosphine as a ligand. By "platinum group metal" we mean platinum, rhodium, palladium, ruthenium, iridium and osmium. We prefer to use a water-soluble complex of rhodium, platinum, ruthenium or palladium, especially rhodium which operates under the mildest conditions. The complex is preferably formed in situ from a water-soluble precursor compound or complex of platinum group metal and a water-soluble phosphine. The choice of precursor compound or complex is not critical to successful operation of the invention. Examples include [Rh(acac)(CO)$_2$], [RhCl$_3$3H$_2$O], [RhCl(diene)]$_2$, [Rh(alkene)$_2$Cl]$_2$, [Rh(diene)$_2$]+A−, [Rh$_2$(C$_5$Me$_5$)$_2$(OH)$_3$]+A−, [Ru$_2$(OH)$_3$(arene)$_2$]+A−, [Pd(allyl)diene]+A−, [Pd$_2$(dba)$_3$]K$_2$[PdCl$_4$], K$_2$[PtCl$_4$], [RuCl$_3$3H$_2$O], Na$_3$[RuCl$_6$] and [Ru$_2$Cl$_4$(arene)$_2$]. In the above, acac represents acetylacetonato, a suitable diene is 1,5-cyclooctadiene, a suitable alkene is cyclooctene, suitable arenes include p-cymene (ie isopropyltoluene) and hexamethylbenzene, A is a non-complexing anion such as tetraphenylborate or tetrafluoroborate, and dba represents dibenzylidene acetone. The aqueous phase also contains the water-soluble phosphine which reacts with the precursor compound or complex to form the desired complex.

As an alternative to in situ formation, the desired complex may be pre-formed. Either way, the complex is understood to be subject to further changes, under hydrogenation reaction conditions, to form the actual catalytically-active species or group of species in dynamic equilibrium one with another, according to various mechanistic schemes which have been published (see, for example, B. R. James, "Homogeneous Hydrogenation", (Wiley), 1974).

Suitable pre-formed complexes include [RhL$_2$(diene)]A, [RhClL$_3$], RuH$_2$(arene), [Ru$_2$(OH)$_3$(arene)$_2$]A, [Pd(allyl)L$_2$]A, [PdL$_2$(solvent)$_2$]$^{2+}$, Pd(CN)$_2$L$_2$, [Pt(allyl)L$_2$]A and [Ir(diene)pyL]A where L is a water-soluble phosphine ligand, A is a non-coordinating anion such as hexafluorophosphate or tetrafluoroborate, py is pyridine and coordinated solvent is acetone. Suitable dienes include 1,5-cyclooctadiene and suitable arenes include p-cyment (p-isopropyltoluene) and hexamethylbenzene. A suitable pre-formed complex which does not include a water-soluble phosphine is u-chloro-u$^2$-dihydro-bis(n$^6$-hexamethylbenzene)ruthenium (II) chloride. This complex may itself also be prepared in situ by treatment of hexamethylbenzene ruthenium dichloride dimer with hydrogen and base (Na$_2$CO$_3$).

The water-soluble phosphine is preferably a hydroxy or carboxytriaryl phosphine having the general formula

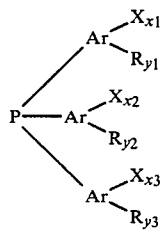

in which the Ar groups are the same or different aryl groups, for example phenyl and naphthyl; the substituent R groups are the same or different and are selected from C$_1$ to C$_4$ linear or branched chain alkyl or alkoxy groups, for example methyl, ethyl, propyl, isopropyl, butyl, methoxy, ethoxy, propoxy or butoxy groups; halogen; hydroxy; nitrile; nitro; amino and C$_1$ to C$_4$ alkyl-substituted amino; the substituent X groups are the same or different and are selected from carboxylic acid, hydroxy, sulphonic acid and salts thereof; x$_1$, x$_2$ and x$_3$ are the same or different integers from 0 to 3 inclusive, provided that at least x$_1$ is equal to or greater than 1; and y$_1$, y$_2$ and y$_3$ are the same or different integers from 0 to 5 inclusive. Preferably Ar is phenyl, X is either COOH or OH, x$_1$ is 1, x$_2$ and x$_3$ are 0 and y$_1$, y$_2$ and y$_3$ are 0. When X is an acid salt, the cation thereof is preferably Na$^+$, although other alkali metal cations such as K$^+$ may alternatively be utilised. Quaternary ammonium cations, for example NH$_4^+$, may also be used.

Preferred water-soluble phosphine include the following compounds:

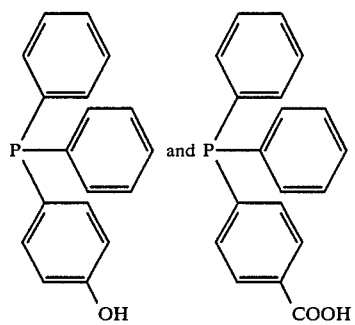

Another example is P(C$_6$H$_4$CO$_2$H)$_3$. Phosphinites of commercially-available polyoxyethylene detergents, for example PPh$_2$(OCH$_2$CH$_2$)$_n$OC$_{12}$H$_{25}$, where n=23, may also be used.

The ratio of the aqueous to organic phases should be in the range 0.33:1 to 5:1, preferably 0.5:1 to 3:1. Good results have been obtained at ratios of approximately 2:1 and 1:1. Lower ratios of aqueous to organic tend to slow the reaction rate whereas higher ratios tend to cause a greater quantity of platinum group metal to accumulate in the organic phase.

The concentration of platinum group metal in the reaction medium is expressed in terms of parts per million (ppm) of metal based on the aqueous phase. We have found that the rate of reaction is increased with increasing platinum group metal concentration to a maximum, after which either a decrease or a tendency to remain the same is observed. Metal concentration should be in the range 100 to 500 ppm; preferably 200–400 ppm, a level of 300 ppm being the optimum in many reactions.

The pH of the aqueous phase should be sufficiently high to solubilise the water-soluble complex. We have found that a pH buffered to 10 is required for a carboxyphosphine-containing complex whereas it is necessary to operate in 0.75M aqueous sodium hydroxide solution, having a pH approaching the maximum, for a hydroxyphosphine-containing complex.

The organic phase consists essentially of the substrate unsaturated organic compound together with hydrogenated product and any by-product formed, with or without one or more organic solvents such as hexane, toluene or chlorobenzene. Suitable unsaturated organic compounds include open-chain (terminal and internal, preferably C$_3$–C$_{20}$) and cyclic olefins, styrene derivatives, polymers such as styrene-butadiene block copolymers (which require selective hydrogenation of the olefinic moieties to improve oxidative stability), aromatics and aldehydes, particularly long chain aldehydes.

The process according to the invention operates under mild conditions of temperature and pressure. The temperature should be in the range 40°–150° C. Too low a temperature results in an unacceptably slow rate of reaction whereas too high a temperature causes complex decomposition and/or catalyst deactivation.

The initial pressure should be within the range 100–10000 kPa, depending on the platinum group metal and the unsaturated organic compound used. For rhodium, the range is 100–3000 kPa, preferably 250–2500 kPa or more preferably 400–600 kPa. The lower pressure limit is determined by the rate of reaction and the upper limit by economic considerations. In other words, the pressure should be as low as possible commensurate with the need to achieve a satisfactory rate.

We have found that, using the process according to the invention, we can achieve an acceptable rate of hydrogenation of the unsaturated organic compound, ideally with low isomerised substrate by-products, the platinum group metal being essentially retained in the aqueous phase and therefore readily separable from the reaction products.

The preferred water-soluble phosphines may be prepared according to the following schemes:

1. 4-Ph$_2$PC$_6$H$_4$CO$_2$H (see G. Schiemenz, Chem. Ber., 1966, 99, 504):

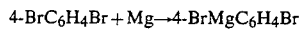

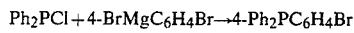

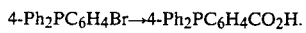

2. 4-Ph$_2$PC$_6$H$_4$OH (see A. E. Senear et al. J.Org.- Chem.1960.25,2001):

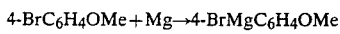

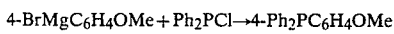

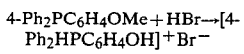

The free ligand may be isolated on treatment with base but hydrobromide may be used per se since the basic conditions required to solubilise it generate the free ligand in situ.

A complex having the general formula RhClL$_3$, which is a preferred rhodium complex, where L is a water-soluble phosphine, may be generated in situ by reaction of three equivalents of ligand per equivalent of rhodium with [Rh$_2$Cl$_2$(coe)$_4$] (where coe=cyclooctene) under an atmosphere of nitrogen. This avoids deactivation due to dimerisation of RhClL$_3$ on storage and was the method used to prepare such complexes in the Examples 1 to 5 which follow.

The invention will now be illustrated with reference to the following Examples and accompanying Tables 1 and 2. In the Tables, runs designated by the capital letters are comparative examples and those designated by Arabic numerals are illustrative of the process according to the invention. Comparative examples are carried out in a two-phase medium without the addition of an amphiphilic reagent. By way of further distinction, in a homogeneous (single phase) medium, the complex or catalytic species is entirely dissolved along with reactants and products. For two-phase media, the catalytic species may become eluted to the organic phase and figures are quoted for this in the Table 1, the balance of the catalytic species remaining in the aqueous phase for ease of separation from the organic. In the absence of figures for elution, the colour of the organic phase provides an indication of the degree of elution.

EXAMPLE 1

Hydrogenation of hex-1-ene

Two-phase hydrogenation runs were carried out using the water-soluble complexes (RhClL$_3$) where L=4-Ph$_2$PC$_6$H$_4$CO$_2$H and 4-Ph$_2$PC$_6$H$_4$OH, both with and without amphiphilic reagent. Using the complex where L=4-Ph$_2$PC$_6$H$_4$CO$_2$H, soluble in pH 10 buffer, the rate of hydrogenation was rather slow but proceeded with quite low levels of isomerisation. The effect of adding amphiphilic reagent was in all cases markedly to increase the rate and the percentage conversion of hex-1-ene, compared with the corresponding two phase system without amphiphilic reagent, although isomerisation was generally increased as well. Nevertheless, the higher percentage conversion overcame the lower selectivity to provide in all cases more of the desired product (hexane) in absolute terms.

Elution of rhodium to the organic phase, determined by atomic absorption analysis, was either unchanged or increased on adding amphiphilic reagent, but for even the worst reagent in this respect (Brij 35), the concentration of rhodium in the organic phase (41.2 ppm) represents only 6.8% by weight of the rhodium added initially.

Using the complex where L=4-Ph$_2$PC$_6$H$_4$OH, soluble in 0.75 m NaOH solution, the rate was fast without amphiphilic reagent although the organic phase became brown in colour, suggesting that at least some catalysis was taking place in the organic. There was also a moderately high rhodium concentration in the organic phase. The addition of amphiphilic reagent actually depressed the rate and in some cases increased the amount of isomerised products, but the reagent sodium lauryl sulphate was beneficial in having a high selectivity to n-hexane coupled with a low rhodium elution, albeit at a low overall conversion.

This reagent looks promising for more elaborate substrates where a high selectivity for hydrogenation with minimum isomerisation is critical.

Conditions of hydrogenation were as follows:

| | |
|---|---|
| [Rh]aq | 300 ppm |
| Hex-1-ene | 109 |
| Aqueous | 20 ml |
| Pressure (initial) | 560 kPa |
| Temperature | 80° C. |

Results are shown in the accompanying Table 1, in which the rate is presented in terms of the time in minutes taken for the pressure to drop from 560 to 520 kPa after the fifth successive pressurisation to 560 kPa.

In Table 1:

"LTAB" is lauryltrimethylammonium bromide.
"CTAB" is cetyltrimethylammonium bromide.
"CTAA" is cetyltrimethylammonium acetate.
"(CTA)$_2$S" is cetyltrimethylammonium sulphate.
"SLS" is sodium lauryl sulphate.

EXAMPLE 2

Hydrogenation of cyclohexene

Using cyclohexene as substrate, isomerisation has no effect on product distribution. The substrate was not particularly susceptible to hydrogenation, with or without amphiphilic reagent, although the addition of the latter did effect an improvement in rate.

Results are shown in the accompanying Table 2 for addition of LTAB to the reaction medium where the water-soluble phosphine in the complex is the carboxy phosphine 4-Ph$_2$PC$_6$H$_4$CO$_2$H (pH 10 buffer) and for addition of SLS to the reaction medium where the phosphine is the hydroxy phosphine, 4-Ph$_2$PC$_6$H$_4$OH (0.75M NaOH). In the absence of amphiphilic reagent, both ligands resulted in a brown organic phase. LTAB increased the rate and markedly reduced elution of rhodium to the organic phase, which was colourless.

The hydroxyphosphine ligand in the absence of amphiphilic reagent caused a higher rate but also a high level of rhodium elution; the presence of SLS increased the rate and also reduced the elution of rhodium, the organic layer being colourless.

Conditions were as follows:

| | |
|---|---|
| [Rh]aq | 300 ppm |
| Cyclohexene | 10 g |
| Aqueous | 20 ml |
| A:Rh | 10:1 |
| Pressure (initial) | 560 kPa |
| Temperature | 80° C. |

EXAMPLE 3

Hydrogenation of α-methylstyrene

The two-phase hydrogenation of α-methyl styrene using the carboxyphosphine ligand gave a better rate without amphiphilic reagent than with it, but the organic phase became yellow, suggesting that catalysis was taking place in the organic phase. The rhodium concentration in the organic phase was 33 ppm. Addition of amphiphilic reagent (LTAB) reduced the rate from a pressure change of 240 kPa/4 h to 110 kPa/4 h but dramatically reduced the rhodium elution to the organic phase (1.8 ppm) which remained colourless.

Conditions were the same as for Example 2.

EXAMPLE 4

Hydrogenation of SBR polymer

In order to improve oxidative stability of styrene-butadiene block copolymers, the olefinic groups should be selectively hydrogenated, leaving the styrene groups unattacked. Conventional homogeneous catalysts have highly selective action but are extremely difficult, if not impossible, to remove from the polymer.

In applying the process of the invention to polymer substrates, we used a styrene-butadiene block copolymer supplied by Aldrich Chemical Co. Ltd. and containing about 30% styrene. This was dissolved in a mixture of ether and cyclohexane and submitted to two-phase hydrogenation. The carboxyphosphine ligand gave no hydrogenation in the absence of amphiphilic reagent. The addition of LTAB yielded 7% olefin hydrogenation with no styrene hydrogenation (as determined by $^1$H NMR spectroscopy). The hydroxyphosphine ligand gave 69% olefin hydrogenation without amphiphilic reagent but 174 ppm rhodium was eluted to the organic. Addition of LTAB (LTAB:Rh 10:1) slightly reduced the olefin hydrogenation (51%) but more than halved the rhodium elution (80 ppm). Addition of LTAB at 20:1 increased the olefin hydrogenation to 58%; the product was a thick yellow emulsion from which the polymer was isolated by pouring into propan-2-ol.

Reaction conditions were the same as for Example 2, the organic phase consisting of 5 g of cyclohexane plus 5 g of a solution formed by dissolving 6 g of polymer in a mixture of ether (10 g) and cyclohexane (40 g).

EXAMPLE 5

Hydrogenation of dodecanal

The homogeneous catalytic hydrogenation of aldehydes cannot be carried out using cationic rhodium complexes which are effective for ketone hydrogenation because the catalysts become deactivated due to carbonyl abstraction. Ruthenium complexes may, however, be used instead.

For two-phase operation using as catalytic complex the compound [RuCl$_2$(L)$_3$], where L is the carboxyphosphine ligand, and obtained from RuCl$_3$ as precursor, there is an increase in rate on raising the temperature or pressure but also an increase in ruthenium elution to the organic phase. Nevertheless, addition of LTAB at a temperature of 110° C. effected an improvement in conversion from 1.9% to 31.5%, selectivity to dodecanol being 100% (the aldol product being the potential by-product). The organic phase is increasingly polar as the reaction proceeds and this is believed to account for the tendency of the ruthenium to become eluted thereto.

Conditions (except for temperature) were as for Example 2.

EXAMPLE 6

Hydrogenation of toluene

Toluene was hydrogenated in a two-phase system using as catalytic complex the compound μ-chloro-μ$^2$-dihydro-bis(n$^6$-hexamethylbenzene)ruthenium(II) chloride having the formula

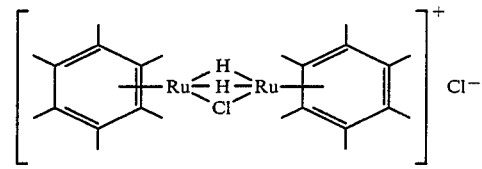

prepared according to the method of Bennett et al, J.Chem. Soc.,Chem. Comm., 1979, 312. Reaction was carried out in a rocking autoclave at 50° C., 5065 kPa H$_2$ for 18 hours.

Using 6 mg (1×10$^{-5}$ mol) of catalyst in water (4 ml)—i.e. 500 ppm (aq)—with toluene (2 ml), 49% conversion to methylcyclohexane was achieved in 18 hours, without added amphiphilic reagent. Addition of 1×10$^{-4}$ moles of each of three amphiphilic reagents (CTAB, SLS and Brij 35) in separate runs increased the yield to 61% and 79% respectively for CTAB and SLS. No significant change was noted for Brij 35.

Aromatic substrates are not readily susceptible to hydrogenation and the amphiphilic reagent SLS gave a significant improvement in yield. The organic phase in each run was colourless.

| Run | Phosphine | Amphiphilic Reagent (A) | A:Rh | Rate ΔP(5) (min) | Conversion % | Sel. to hexane % | Sel. to t-hex-2-ene % | Sel. to c-hex-2-ene | Color of organic phase | [Rh] organic ppm |
|---|---|---|---|---|---|---|---|---|---|---|
| A | CO$_2$H | none | — | 20 | 42 | 73 | 14 | 13 | colourless | <0.5 |
| 1 | " | LTAB | 5:1 | 5 | 93 | 50 | 27 | 23 | colourless | <0.5 |
| 2 | " | LTAB | 10:1 | 6 | 94 | 39 | 37 | 25 | colourless | <0.5 |
| 3 | " | CTAB | 10:1 | 6 | 99 | 41 | 40 | 19 | colourless | 1.2 |
| 4 | " | CTAA | 10:1 | 9 | 99 | 43 | 35 | 21 | colourless | 0.5 |

-continued

| Run | Phosphine | Amphiphilic Reagent (A) | A:Rh | Rate $\cdot \Delta P(5)$ (min) | Conversion % | Sel. to hexane % | Sel. to t-hex-2-ene % | Sel. to c-hex-2-ene | Color of organic phase | [Rh] organic ppm |
|---|---|---|---|---|---|---|---|---|---|---|
| 5 | " | (CTA)$_2$S | 10:1 | 8 | 98 | 36 | 43 | 22 | colourless | <0.5 |
| 6 | " | Brij 35 | 10:1 | 6 | 100 | 40 | 49 | 12 | colourless | 41.2 |
| 7 | " | Bu$_4$N$^+$Cl$^-$ | 4:1 | 3 | 100 | 44 | 40 | 15 | colourless | 4.3 |
| 8 | " | Bu$_4$N$^+$Cl$^-$ | 10:1 | 6 | 98 | 50 | 35 | 15 | pale yellow | — |
| 9 | " | Bu$_4$N$^+$OH$^-$ | 4:1 | 0.75 | 100 | 57 | 33 | 10 | colourless | — |
| 10 | " | Bu$_4$N$^+$OH$^-$ | 4:1 | 6 | 65 | 62 | 20 | 18 | colourless | <0.5 |
| 11 | " | Bu$_4$N$^+$OH$^-$ | 4:1 | 7 | 100 | 64 | 27 | 9 | pale yellow | 3.6 |
| 12 | " | Bu$_4$N$^+$OH$^-$ | 10:1 | 3 | 100 | 65 | 27 | 9 | pale yellow | 20.4 |
| B | OH | none | — | 4 | 95 | 48 | 36 | 19 | brown | 20 |
| 13 | " | LTAB | 10:1 | 7 | 99 | 37 | 50 | 13 | pale yellow | 19.6 |
| 14 | " | Brij 35 | 10:1 | 7 | 99 | 36 | 50 | 14 | pale yellow | 10.8 |
| 15 | " | SLS | 10:1 | 5 | 45 | 79 | 13 | 8 | colourless | 0.5 |
| 16 | " | Bu$_4$N$^+$OH$^-$ | 10:1 | 8 | 44 | 13 | 19 | 19 | colourless | 1.0 |

TABLE 2

| Run | Ligand | Amphiphilic reagent (A) | P/time |
|---|---|---|---|
| C | CO$_2$H | — | 60 kPa/5h |
| 17 | " | LTAB | 60 kPa/3h |
| D | OH | — | 200 kPa/3h |
| 18 | " | SLS | 200 kPa/2h |

We claim:

1. A catalytic process for the hydrogenation of an unsaturated organic compound selected from (a) the group consisting of open-chain olefins having from 3 to 20 carbon atoms and cyclic olefins to produce the corresponding alkene, (b) styrenes to produce the corresponding alkyl benzenes, (c) styrene-butadiene copolymers to selectively hydrogenate the olefinic groups, and (d) aliphatic aldehydes to produce the corresponding alcohols comprising reacting together the said compound and hydrogen in the presence of a catalyst comprising a water-soluble complex of a platinum group metal containing as a ligand therein a water-soluble phosphine selected from carboxy-triaryl phosphines and hydroxy-triaryl phosphines in a reaction medium comprising an aqueous phase and an organic phase, wherein the reaction medium also includes an amphiphilic reagent, the aqueous phase contains the catalyst and the organic phase contains the said compound, the amphiphilic reagent containing polar and non-polar moieties and being substantially soluble in the aqueous phase and substantially insoluble in the organic phase, the reaction temperature being in the range 40°–150° C., the initial reaction pressure being in the range 100–10,000 kPa, the pH of the aqueous phase being sufficiently high to solubilize the water-soluble complex, the ratio of aqueous phase to organic phase being in the range 0.33 to 5:1, the concentration of amphiphilic reagent to platinum group metal being up to 100:1 on a molar basis and the concentration of the platinum group metal being in the range 100 to 500 ppm based on the aqueous phase.

2. A process according to claim 1 wherein the molar concentration of amphiphilic reagent relative to the platinum group metal is within the range from 1:1 to 25:1.

3. A process according to claim 1 wherein the water-soluble complex is a complex of rhodium, platinum, ruthenium or palladium.

4. A process according to claim 1 wherein the complex is formed in situ.

* * * * *